US008114963B2

(12) United States Patent
Bell et al.

(10) Patent No.: US 8,114,963 B2
(45) Date of Patent: *Feb. 14, 2012

(54) FLUORESCENT COMPOUNDS

(75) Inventors: Philip John Livingston Bell, Turramurra (AU); Peter Karuso, Epping (AU)

(73) Assignee: Flurotechnics Pty Limited, North Ryde (AU)

( * ) Notice: Subject to any disclaimer, the term of this patent is extended or adjusted under 35 U.S.C. 154(b) by 1043 days.

This patent is subject to a terminal disclaimer.

(21) Appl. No.: 11/949,525

(22) Filed: Dec. 3, 2007

(65) Prior Publication Data

US 2008/0085993 A1    Apr. 10, 2008

Related U.S. Application Data

(62) Division of application No. 10/258,310, filed as application No. PCT/AU01/00472 on Apr. 26, 2001, now abandoned.

(30) Foreign Application Priority Data

Apr. 26, 2000    (AU) ..................... PQ7117

(51) Int. Cl.
*C07K 1/00* (2006.01)
*C07K 1/13* (2006.01)
*C07D 307/93* (2006.01)
*C07D 307/00* (2006.01)

(52) U.S. Cl. ......... 530/363; 530/364; 549/299; 549/301

(58) Field of Classification Search .................. 530/363, 530/364; 549/299, 301
See application file for complete search history.

(56) References Cited

U.S. PATENT DOCUMENTS

| 3,993,789 | A | | 11/1976 | Moll et al. | |
| 5,013,565 | A | * | 5/1991 | St. Martin et al. | ............ 426/250 |
| 6,046,022 | A | | 4/2000 | Zhang et al. | |
| 7,713,694 | B2 | * | 5/2010 | Mackintosh et al. | ............. 435/6 |

FOREIGN PATENT DOCUMENTS

| EP | 1 223 226 A2 | 7/2002 |
| WO | WO 98/31824 | 7/1998 |
| WO | WO 01/81351 A1 | 11/2001 |
| WO | WO 02/40595 A1 | 5/2002 |

OTHER PUBLICATIONS

International Search Report, PCT/AU01/00472, Australian Patent Office as Searching Authority, Jun. 4, 2001.
Fielding et al., "The Chemistry of Fungi, Part XXXIX. The Structure of Monascin.," *J. Chem. Soc.*, 1961:4579-4588 (1961).
Zhang et al., "Studies on Edible Red Pigment II, Experiments in Larger Scale Fermenter and Extraction Technology of Red Pigment," *Shipin Yu Faxiao Gongyo*, 5:21-26 (1982). Chinese language document with English abstract, pp. 21-26, Abstract Only.
Bartoszek, et al.: "Versatile method employing basic techniques of genetic engineering to study the ability of low-molecular weight compounds to bind covalently with DNA in cell-free systems," *Analytical Biochemistry 313*: 53-59 (2003).
Bathale, et al.: "Energetic and binding properties of DNA upon interaction with dodecyl trimethylammonium bromide," *Nucleic Acids Research 27* (4); 1001-1005 (1999).
Bell, et al.: "Epicocconone, A Novel Fluorescent Compound from the Fungus *Epicoccum nigrum*," *J. Am. Chem. Soc. 125*: 9304-0305 (2003).
Bhairi, S.: *Detergents: A guide to the properties and uses of detergents in biological systems*, Calbiochem-Novabiochem Corporation, 2001.
Breadmore, et al.: "Microchip-Based Purification of DNA from Biological Samples," *Anal. Chem. 75*: 1880-1886 (2003).
Chen et al., "The Chemistry of Fungi. Part LXIV. The Structure of Monascin: The Relative Stereochemistry of the Azophilones," *J. Chem Soc.*, pp. 3577-3579 (1971).
European Search Report for EP 01925207, dated Mar. 2, 2004.
Ferrari, et al.: "Application of the novel fluorescent dye Beljian red to the differentiation of *Giardia* cysts," *Journal of Microbiological Methods 52*: 133-135 (2003).
Fielding et al., "Fungi—(XXXIX) Structure of Monascin," *Chemical Abstracts*, 56:8677c, 1962.
Graczyk, et al.: "Detection of *Cryptosporidium parvum* and *Giarsia lamblia* Carried by Synanthropic Flies by Combined Fluorescent In Situ Hybridization and a Monoclonal Antibody," *Am. J. Trop. Med. Hyg. 68*(2): 228-232 (2003).
Hadfield et al., "Biosynthesis of Fungal Metabolites. II. β-Oxo-lactone Equivalents in Rubropunctatin and Monascorubrin," *J. Chem. Soc.*, 8:751-755 (1967).
Harrington, et al.: "Binding to the yeast Swi4,6-dependent cell cycle box, CACGAAA, is cell cycle regulated in vivo," *Nucleic Acids Research 24*(4): 558-565 (1996).
Haws et al., "Fungi—(XXVII) Structure of Rubropunctatin," *Chemical Abstracts*, 54:7968g, 1960.
Haws et al., "The Chemistry of Fungi. Part XXXVII. The Structure of Rubropinctatin," *J. Chem. Soc.*, pp. 3598-3610 (1959).
Inouye et al., "Structure of Monascoflavin," *Tetrahedron*, 18:1195-1203 (1962).
International Preliminary Examination Report for corresponding PCT.AU2004/000370 dated Jul. 5, 2005.
International Search Report for corresponding PCT/AU2004/000370 dated Jul. 19, 2004.
International Search Report for PCT/AU01/00472, dated Jun. 4, 2001.

(Continued)

*Primary Examiner* — Jon P Weber
*Assistant Examiner* — Kailash C Srivastava
(74) *Attorney, Agent, or Firm* — Marshall, Gerstein & Borun LLP

(57) ABSTRACT

Fluorescent dye compounds of formula (I) are disclosed. These compounds are useful as they interact with organic compounds in a manner such that excitation with certain wavelengths of light results in fluorescent emission. Detection and/or monitoring of the fluorescence provides a means for the detection or quantification of organic compounds when bound to these fluorescent dye compounds. Formula (I), wherein: each of R, R' and R" is a hydrogen atom, halogen atom or a straight or branched $C_{1-20}$ alkyl, alkenyl or alkynl group optionally substituted with one or more halogen, hydroxyl, and/or oxy group; rings A, B and C optionally include one or more double bonds; rings B and C are optionally substituted with one or more halogen atoms.

2 Claims, 2 Drawing Sheets

OTHER PUBLICATIONS

Jaroszeski, et al.: "Detection and Quantitation of Cell-Cell Electrofusion Products by Flow Cytometry," *Analytical Biochemistry* 216: 271-275 (1994).

Kamp, et al.: "Rapid Flip-flop of Oleic Acid across the Plasma Membrane of Adipocytes," *The Journal of Biological Chemistry* 278(10): 7988-7995 (Mar. 7, 2003).

Kersten, et L.: "Generation of *Arabidopsis* protein chips for antibody and serum screening," *Plant Molecular Biology* 52: 999-1010 (2003).

Kumasaki et al., "Structure of Monascorubrin," *Tetrahedron*, 18:1171-1184 (1962).

Manchand et al., "Isolation and Structure of Ankaflavin: A New Pigment from *Monascus anka*," *Phytochem.*, 12:2531-2532 (1973).

Martinkova et al., "Biological Activities of Oligoketide Pigments of *Monascus purpureus*," *Food. Addit. Contam.*, 16(1):15-24 (1999).

Natsume et al., "Chlamydospore-like Cell-inducing Substances of Fungi: Close Correlation between Chemical Reactivity with Methylamine and Biological Activity," *Agric. Biol. Chem.*, 52(2):307-312 (1988).

Ohashi et al., "Mass Spectra of the Metabolites of Monascus," *Shitsuryo bunseki*, 15(3-4):188-197 (1967).

Paulmurugan, et al.: "Molecular Imaging of Drug-Modulated Protein-Protein Interactions in Living Subjects," *Cancer Research* 64: 2113-2119 (Mar. 15, 2004).

Shapiro, H.: *Practical Flow Cytometry*, 4th ed. Wilet-Liss, Hoboken, NJ, 2003.

Stadler et al., "Novel Bioactive Azaphilones from Fruit Bodies and Mycelial Cultures of the Ascomycete Bulgaria inquinans," *Natural Product Research*, 7:7-14 (1995).

STN File Registry RN 13283-85-7, entered STN Registry Nov. 16, 1984.

STN File Registry RN 31187-25-4, entered STN Registry Nov. 16, 1984.

STN File Registry RN 3733-70-8, entered STN Registry Nov. 16, 1984.

STN File Registry RN 52922-45-9, entered STN Registry Nov. 16, 1984.

STN File Registry RN 52922-46-0, entered STN Registry Nov. 16, 1984.

STN File Registry RN 52922-47-1, entered STN Registry Nov. 16, 1984.

Tomoda et al., "Structure-specific Inhibition of Cholesteryl Ester Transfer Protein by Azaphilones," *Journal of Antibiotics*, 52(2):160-70 (1999).

Whalley et al., "The Chemistry of Fungi. Part LXVIII. The Absolute Configuration of (+)—Sclerotiorin and the Azaphilones," *J. Chem. Soc.*, 13:1366-1369 (1976).

Zhang et al., "Studies on Edible Red Pigment II, Experiments in Larger Scale Fermenter and Extraction Technology of Red Pigment," *Shipin Yu Faxiao Gongyo*, 5:21-26 (1982).

Ohashi et al., Monascorubrin. L "Momascaminone", A Degradation Product, *Journal of American Chemical Society*, 6339 (Dec. 5, 1959).

Nakanishi et al., "Monascorubrin IL1 Structures of Monascorubrin and Monascamine," *Journal of American Chemical Society*, 6339-6340 (Dec. 5, 1959).

\* cited by examiner

FLUORESCENT COMPOUNDS

RELATED APPLICATION DATA

This application is a divisional of U.S. application Ser. No. 10/258,310, filed Feb. 24, 2003 as the U.S. National Phase of PCT/AU01/000472, filed Apr. 26, 2001 and claiming the benefit of priority to PQ 7117 AU filed Apr. 26, 2000.

TECHNICAL FIELD

This invention relates generally to novel fluorescent compounds and to compounds which can function as fluorescent dyes, methods of isolating such compounds from microorganisms and uses of such compounds in scientific applications.

BACKGROUND ART

Compounds that fluoresce have many uses and are known to be particularly suitable for biological applications where fluorescence is required for the detection of whole cells, cellular components, and cellular functions. For example, many diagnostic and analytical techniques require the samples to be fluorescently tagged so that they can be detected. This is achieved by using fluorescent dyes or probes which interact with a wide variety of materials such as cells, tissues, proteins, antibodies, enzymes, drugs, hormones, lipids, nucleotides, nucleic acids, carbohydrates, or natural or synthetic polymers to make fluorescent conjugates.

With synthetic fluorescent probes, ligands are frequently used to confer a specificity for a biochemical reaction that is to be observed and the fluorescent dye provides the means of detection or quantification of the interaction. These applications include, among others, the detection of proteins (for example in gels or aqueous solution), cell tracking, the detection of proteins via fluorescently labelled antibodies, the assessment of enzymatic activity, the staining of nucleic acids.

Long wavelength absorbance usually increases the utility of a fluorescent probe since it reduces the interference from cellular auto-fluorescence and reduces the cytotoxic effect of the fluorophore in combination with light. Although lasers are particularly useful as a concentrated light source for the excitation of fluorescence, at present the output of lasers is restricted to particular wavelengths of light. Compounds whose excitation spectra coincide with laser output are therefore of high utility. The argon laser is the most common light source for excitation of fluorescence, and has principal outputs, light at 488 nm and 514 nm. Fluorescent compounds that are excited by either of these wavelengths are therefore of particular utility. Alternatively, excitation of fluorescence can be achieved using solid state light sources such as Light emitting diodes. Fluorescent compounds excited by the light emitted from these alternative sources are also of particular utility.

Red fluorescent compounds are used extensively in many fields of biological study. Many of these, including Texas red, Tetramethyl rhodamine-isothiocyanate or red emitting BODIPY dyes require excitation at green wavelengths such as 542 nm. This limits their use in many applications, especially those where the argon-ion laser is used for excitation. Compounds such as ethidium bromide, can be excited with light from the argon-ion laser (520 nm band), but are not generally suitable for tagging of organic molecules other than nucleic acids. Other compounds such as phycoerythrin, can be excited using the argon-ion laser (488 nm) and does emit in the orange/red wavelengths. Phycoerythrin, however, has poor stability and a high molecular weight making it unsuitable for many applications such as cell tracking, labelling of nucleic acids or staining proteins.

For staining of proteins, there are a number of methods available. These methods can utilise non-fluorescent compounds, or fluorescent compounds. The most commonly used method utilises Coomassie blue which is non-fluorescent, can require the use of large amounts of organic solvents and is time consuming. Other fluorescence-based protein-detection methods are available which are potentially more sensitive than non-fluorescent methods. However, these methods are in general much more expensive than non-fluorescent methods which limits their widespread use. Therefore, compounds that combine useful spectral characteristics, and relatively high sensitivity will be of particular utility.

There are several methods for the quantification of protein in solution. These methods are based on a range of techniques, and include methods where dyes bind to soluble proteins. These dyes can be either non-fluorescent or fluorescent compounds. Fluorescent dye-based methods are often more sensitive than the non-fluorescent dyes, and allow for the determination of protein concentration over a wide range of concentrations. Compounds that combine useful spectral characteristics with an ability to bind proteins will be of particular utility.

In enzymatic studies, there is widespread use of fluorescent compounds for the detection of particular enzymatic activities. For example, fluorescein di-β-D-galactopyranoside (FDG) is a non-fluorescent compound that is sequentially hydrolysed by the enzyme .β.-galactosidase first to generate fluorescein monogalactoside and then to fluorescein which is highly fluorescent. The cleavage of the FDG compound can be monitored by the increase in fluorescence in the solution, and thus allows sensitive quantification of enzymatic activity. At present, only a limited number of fluorophores are suitable for this procedure. Therefore, novel fluorescent compounds that can be conjugated to a variety of substrates will be of utility.

For dual colour staining, there is a very limited choice of low molecular weight fluorophores. The predominant green fluorophore is fluorescein, which strongly absorbs light from the 488 nm band of the argon ion laser, and re-emits at 518 nm. At present there are few compatible red or orange fluorophores that are of low molecular weight and are excited by the 488 nm or 514 nm bands of the argon ion laser. Therefore, low molecular weight compounds that are excited by argon ion lasers and emit at wavelengths greater than 600 nm will be of utility, particularly if there is minimal spectral overlap with fluorescein.

The present inventors have isolated new compounds derived from a fungus that is capable of combining readily with a range of organic molecules to produce fluorescent complexes.

DISCLOSURE OF INVENTION

In a first aspect of the invention, there is provided a compound according to formula (I):

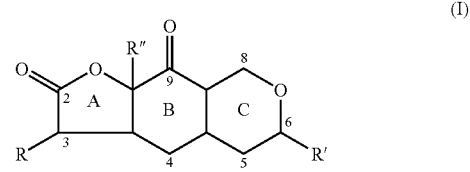

wherein:

each of R, R' and R'' is a hydrogen atom, halogen atom or a straight or branched chain $C_{1-20}$ alkyl, alkenyl or alkynyl group optionally substituted with one or more halogen, hydroxy and/or oxy group;

rings A, B and C optionally include one or more double bonds;

rings B and C are optionally substituted with one or more halogen atoms; and the compound is capable of interacting with an organic compound and when interacting with the organic compound, the compound emits fluorescence after excitation at a broad range of wavelengths. Preferably, the compound is excited at wavelengths in the range of 300-560 nm, more preferably, 380-530 nm and even more preferably, UV wavelengths and/or blue wavelengths. Preferably the compound emits in the wavelengths of 460 to 700 nm. More preferably its emission peak is centered around 530 nm when interacting with an organic compound such as sodium dodecyl sulphate and centered around 605 nm when interacting with a biomolecule such as a protein or cell.

Preferably, the first aspect of the invention provides a compound according to formula (Ia):

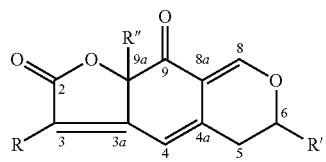

(Ia)

Preferably, the compound according to formula Ia has the stereochemistry as depicted in formula (Ib):

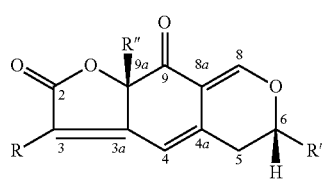

(Ib)

Preferably, R is a straight or branched chain $C_{1-20}$ conjugated alkenyl group optionally substituted with hydroxy and oxy groups; R' is a straight or branched chain $C_{1-20}$ alkyl group optionally substituted with a hydroxy group and R'' is a straight or branched chain $C_{1-20}$ alkyl group.

More preferably, R=—C(OH)CHC(O)(CH)$_6$CH$_3$, R'=—CH$_2$OH and R''=Me such that the present invention according to the first and second aspects consists in the compound 5,6-dihydro-3-[(1Z,4E,6E,8E)-1-hydroxy-3-oxo-1,4,6,8-decatetraenyl]-6-hydroxymethyl-9a-methyl-2H-f-uro[3,2-g][2]benzopyran-2-9(9aH)-dione according to formula (Ic):

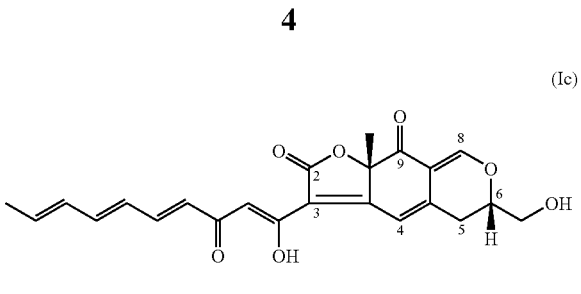

(Ic)

In a second aspect, the present invention consists in a compound according to formula (I), wherein each of R, R' and R'' is a hydrogen atom, halogen atom or a straight or branched chain $C_{1-20}$ alkyl, alkenyl or alkynyl group optionally substituted with one or more halogen, hydroxy and/or oxy groups;

ring A, B and C are optionally substituted with one or more halogen atoms; and rings A, B and C optionally include one or more double bonds; with the proviso that:

(i) R≠—C(OH)CHC(O)(CH)$_6$C(Et)(Me) when R'=—CH$_2$OH, R''=Me, ring A includes a double bond between C3 and C3a; ring B includes a double bond between C4 and C4a; and ring C includes a double bond between C8 and C8a;

(ii) R≠—C(OH)CHC(O)(CH)$_6$C(Et)(Me) when R'=Me, R''=Me, ring A includes a double bond between C3 and C3a; ring B includes a double bond between C4 and C4a; and ring C includes a double bond between C8 and C8a;

(iii) R≠—C(OH)CHC(O)(CH)$_6$C(Et)(Me) when R'=Me, R''=Me, ring A includes a double bond between C3 and C3a; ring B includes a double bond between C4 and C4a; and ring C includes a double bond between C8 and C8a and C5 and C6;

(iv) R≠—C(O)(CH)$_4$Me when R'=-n-propyl, R''=Me, ring A includes a double bond between C3 and C3a; ring B includes a double bond between C4 and C4a; and ring C includes a double bond between C8 and C8a and C5 and C6;

(v) R≠—C(O)(CH)$_6$Me when R'=-n-propyl, R''=Me, ring A includes a double bond between C3 and C3a; ring B includes a double bond between C4 and C4a; and ring C includes a double bond between C8 and C8a and C5 and C6;

(vi) R≠—C(O)(CH$_5$Me when R'—(CH)$_2$Me, R''=Me, ring A includes a double bond between C3 and C3a; ring B includes a double bond between C4 and C4a; and ring C includes a double bond between C8 and C8a and C5 and C6;

(vii) R≠—C(O)(CH)$_6$Me when R'—(CH)$_2$Me, R''=Me, ring A includes a double bond between C3 and C3a; ring B includes a double bond between C4 and C4a; and ring C includes a double bond between C8 and C8a and C5 and C6;

(viii) R≠—(CH)$_2$C(Me)CHC(Me)(Et) when R'=—Ac, R''=Me, C4=C1, ring A includes a double bond between C3 and C3a; ring B includes a double bond between C4 and C4a; and ring C includes a double bond between C8 and C8a and C5 and C6;

(ix) R≠—(CH$_2$C(Me)CHC(Me)(Et) when R'—Ac, R''=Me, ring A includes a double bond between C3 and C3a; ring B includes a double bond between C4 and C4a; and ring C includes a double bond between C8 and C8a and C5 and C6;

(x) R≠—(CH)$_2$(Me)CH-i-Pr when R'=—Ac, R''=Me, ring A includes a double bond between C3 and C3a; ring B includes a double bond between C4 and C4a; and ring C includes a double bond between C8 and C8a and C5 and C6;

(xi) R≠—C(O)(CH)$_4$Me when R'=—(CH)$_2$Me, R''=Me, ring A includes a double bond between C3 and C3a; ring B includes a double bond between C4 and C4a; and ring C includes a double bond between C8 and C8a and C5 and C6;

(xii) R≠—C(O)(CH)₄Me when R'=-n-Pr, R"=Me, ring A does not include a double bond; and rings B and C include double bonds between C8a and C4a and C5 and C6;

(xiii) R≠—C(O)(CH)₄4Me when R'=-n-Pr, R"=Me, ring A, B and C do not include double bonds;

(xiv) R≠—C(O)(CH₆,Me when R'=—(CH)₂Me, R"=Me, ring A does not include a double bond; and rings B and C include double bonds between C8a and C4a and C5 and C6;

(xv) R≠—C(O)(CH)₄Me when R'=—C(CH₂)(Me), R"=Me, ring A does not include a double bond; and rings B and C include double bonds between C8a and C4a and C5 and C6;

(xvi) R≠—C(O)(CH)₄Me when R'=—(CH)₂Me, R"=Me, ring A does not include a double bond; and rings B and C include double bonds between C8a and C4a and C5 and C6.

Preferably, the compound according to second aspect of the invention is in accordance with formula (Ia) and more preferably, has the stereochemistry as depicted in formula (Ib).

Even more preferably, R=—C(OH)CHC(O)(CH)₆CH₃, R'=—CH₂OH and R"=Me such that the present invention according to the second aspect consists in the compound 5,6-dihydro-3-[(1Z,4E,6E,8E)-1-hydroxy-3-oxo-1,4,6,8-decatetraenyl]-6-hydroxymethyl-9a-methyl-2H-f-uro[3,2-g][2]benzopyran-2-9(9aH)-dione according to formula (Ic).

It will be appreciated that the compound according to formula (I)-(Ic) includes all corresponding tautomeric structures.

Chemically, the compounds of formula (I)-(Ic), such as 5,6-dihydro-3-[(1Z,4E,6E,8E)-1-hydroxy-3-oxo-1,4,6,8-decatetraenyl]-6-hydroxymethyl-9a-methyl-2H-furo[3,2-g][2]benzopyran-2-9(9aH)-dione, are members of the azaphilone compounds. The azaphilone compounds are produced by a variety of fungi, and have been investigated for their antibiotic functions, their ability to inhibit enzymatic function, and their role as colouring agents in the food additives produced by *Monascus* sp.

The azaphilone nucleus has also been found in the pigments produced by *Monascus* sp. The pigments containing the common azaphilone core include dihydro-monascin and monascorubin. There is no record of their utility as fluorescent dyes for the staining of biomolecules or organic compounds.

None of the prior art known to the applicant teaches or suggests that a compound of the structure described in formula (I)-(Ic) would be fluorescent, nor suggests that it would be suitable for use in the fluorescent staining of bio-molecules or organic compounds. There are accordingly unexpected and advantageous properties associated with this compound including sensitive detection of proteins in gels, cell tracking and dual colour staining.

The present inventors have unexpectedly found that compounds according to formula (I)-(Ic) are not fluorescent in aqueous solution, but are capable of interacting with organic compounds to produce an intensely fluorescent stain. In a preferred embodiment, the compounds according to formula (I)-(Ic) of the invention are used in the detection and tagging of organic molecules.

Preferably, the compound according to formula (I)-(Ic), when bound to an organic molecule emits fluorescence after excitation at blue wavelengths. More preferably, the compounds according to formula (I)-(Ic) are excited by light in the absorbance range 300-560 mm.

In a preferred embodiment, a compound according to formula (I)-(Ic) interacts with proteins to produce a fluorescent complex that can be excited by light generated by standard UV transilluminators (307 nm). Upon excitation, the fluorescent complex emits light over a wide range of wavelengths allowing the protein complexes to be detected. The excitation wavelength of the protein/dye complex includes that of ethidium bromide complexed with DNA (Absorption maximum 518 nm, Emission maxima 605 nm). This is of particular utility because it allows the same equipment to be used to detect both DNA and protein in gels. The broad range of excitation wavelengths allows the compound to be excited strongly by 488 nm and 514 nm bands of the argon ion laser, as well as absorb light emitted from diode light sources such as those the emit at around 400 nm In another preferred embodiment, a fluorescent form of the compound according to formula (I)-(Ic) is capable of strongly absorbing light from the 488 n output of the argon-ion laser, and to re-emit the light at wavelengths longer than 600 nm.

In another preferred embodiment, the compound according to formula I is included in a composition, along with an analytically acceptable carrier, and may be used in combination with a fluorochrome such as fluorescein in dual staining applications. Such a fluorochrome may be included in the composition or separately used.

The compound according to formula (I)-(Ic) may be produced by a fungal species. Preferably, the fungal species is the strain deposited at the Australian Government Analytical Laboratories (AGAL) on Jan. 15, 1998 identified by Accession Number NM98/00507.

The methods for purification, isolation, as well of the structure of the novel fluorophore 5,6-dihydro-3-[(1Z,4E,6E,8E)-1-hydroxy-3-oxo-1,4,6,8-decatetraenyl]-6-hydroxymethyl-9a-methyl-2H-f-uro[3,2-g][2]benzopyran-2-9(9aH)-dione and related compounds have not previously been described.

The binding of the compound according to formula (I)-(Ic) to organic molecules may involve direct chemical or physical binding or may be achieved by the use of "linking molecules" known to the art. Organic molecules which may be bound by the compound of the invention when used as a fluorescent dye include, for example, proteins, peptides, sugars, nucleic acids, antibodies, cell surface biomolecules, detergents and cells. Due to the compound's fluorescent and organic compound-binding characteristics, it will be appreciated that the compound will have use in any application where detection of a fluorescent dye attached to an organic compound is required.

In a third aspect, the present invention consists in a process of producing a compound according to the first and second aspect of the invention, the process comprising culturing a fungal species under conditions such that the fungal species produces the compound; and separating the compound from the culture.

The compound according to formula (I)-(Ic) can be used as a fluorescent dye when in a crude culture extract or when purified by extraction and separation techniques.

It has been found by the present inventors that after inoculation and incubation of the strain identified by AGAL Accession Number NM98/00507 on the growth medium, a compound which is suitable as a fluorescent dye is produced by the fungus. It will be appreciated that it should be possible to produce compounds according to formula (I)-(Ic) of the first and second aspect of the present invention by using techniques other than from the supernatant of a suitable fungal culture. For example, if the fungus produces a "pre-cursor", then it will be possible to modify that pre-cursor to its fluorescent form by chemical, physical or enzymatic means. The knowledge that such compounds can be obtained from microorganisms should allow the discovery and production of other compounds suitable for use as fluorescent dyes belonging to the same family or quite distinct compounds with useful characteristics. The compound according to formula I may also be produced synthetically by direct chemical synthesis, or by modification of intermediate(s) in the biosynthetic pathway used by the fungi.

The compound according to formula (I)-(Ic) of the present invention may also be produced synthetically by chemical means. The knowledge that a new fluorescent compound is produced by fungi may lead to other means of producing the compound apart from culturing the fungi under the required conditions.

The compound according to formula (I)-(Ic) of the present invention has the distinct advantage that it binds to cells and other organic molecules in its fluorescent form so can be used as a means to track the cells or the other organic molecules when labelled with the compound.

In a fourth aspect, the present invention consists in use of the compound according to the first and second aspect of the present invention as a fluorescent dye or marker, preferably in scientific techniques for staining, labelling and/or detecting organic molecules.

Examples of the use of the compound according to the first and second aspect of the present invention include but are not restricted to cell tracking dyes for microscopy, membrane fluidity dyes, conjugation with antibodies, conjugation to nucleic acids, cell surface ligand imaging dyes, conjugation to sugars, cytometric analysis, and confocal microscopy. It will be appreciated, however, that the compound would be suitable for any use where fluorescence in the red wavelengths is required, including when excited at 488 nm.

In a fifth aspect, the present invention consists in a method of fluorescent-labelling an organic compound, the method comprising causing the compound according to the first or second aspect of the present invention to bind to an organic compound such that the organic compound is fluorescently labelled with the compound.

Preferably, the fluorescently labelled organic compound is detected when exposed to a wide range of wavelengths, preferably wavelengths in the range of 300-560 nm.

The organic compound may include, but is not limited to, proteins, peptides, sugars, nucleic acids, antibodies, cell surface biomolecules, detergents and cells. The compound may bind directly to the organic compound due to a chemical or physical association or may bind to the organic compound via a linking molecule. If the compound is attached to a ligand specific for the organic compound, for example an antibody or lectin, then the binding of that ligand to the organic compound will cause the organic compound to be fluorescently labelled.

In a sixth aspect, the present invention consists in a method of detecting a organic compound in a sample including the organic compound, the method comprising labelling the organic compound according to the method of the fifth aspect of the present invention; and detecting the organic compound in the sample by monitoring or detecting its fluorescence. Preferably, the labelled organic compound is detected when the sample is exposed to light from a wide range of wavelengths, preferably wavelengths in the range of 300-560 nm, more preferably blue wavelengths.

The monitoring or detecting of the fluorescence of the labelled-organic compound may be by any means known to the art. Such means include, but not limited to, transillumination, spectroscopy microscopy and cytometry.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood a preferred forms will be described with reference to the following examples and accompanying drawings.

MODES FOR CARRYING OUT THE INVENTION

EXAMPLE 1

Figure 1:
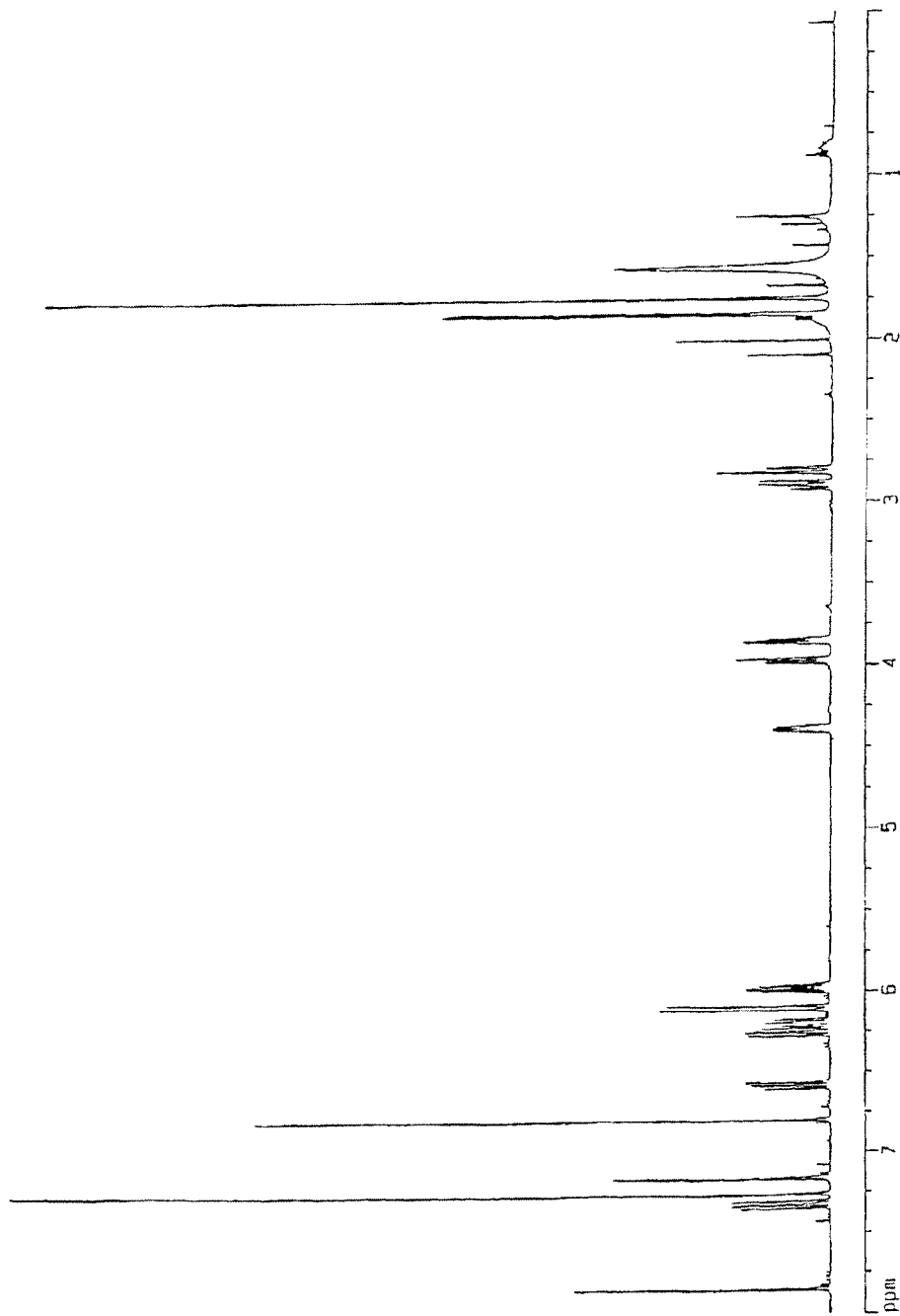
FIG. 1 shows an NMR spectrum of 5,6-dihydro-3-[(1Z,4E,6E,8E)-1hydroxy-3-oxo-1,4,6,8-decatetraenyl]-6-hydroxymethyl-9a-methyl-2H-fu-ro[3,2-g][2]benzopyran-2-9(9aH)-dione a fluorescent compound according to the first and second aspects of the invention.
Figure 2:
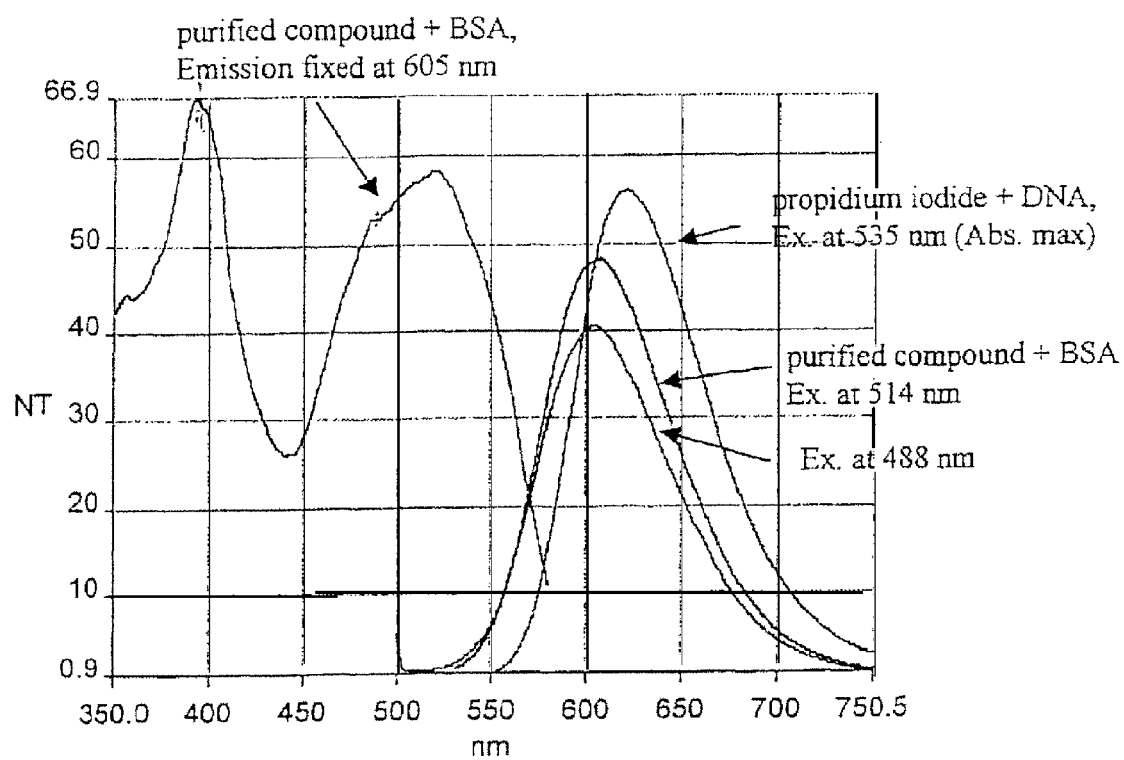
FIG. 2 shows an example of an emission spectra of the compound identified by FIG. 1 when bound to bovine serum albumin (BSA) and propidium iodide bound to DNA. The number of moles of the purified compound used to bind to excess BSA, were equal to the number of moles of propidium iodide used to bind to excess DNA. There are two excitation bands resulting in emission at 605 nm. As seen, excitation by light at 390-400 nm results in maximum emission of light at 605 nm.

Production of Extract A.

A biologically pure culture of the micro-organism having all of the identifying characteristics of the strain identified by AGAL Accession Number NM 98/00507 was obtained.

A growth medium for the fungus, AGAL Accession Number NM 98/00507, was prepared by adding 40 g Sucrose (CSR), 5 g Yeast Extract (Difco), 10 g Peptone (Difco) and 10 g Agar (Difco) to 1 L of water. The mixture was autoclaved for 15 min at 115 .degree. C. to both sterilise the medium and to dissolve the agar. The liquid was poured into culture dishes and allowed to set at room temperature. After cooling, a culture of the fungus was inoculated onto the surface of the medium, and incubated at 25 .degree. C. for three days. The culture was transferred to a refrigerator and incubated at 4 .degree. C. until the culture turned an intense red colour and dye production was high (usually 3 to 5 days).

Once the culture produced sufficient dye for harvesting, the culture medium, including the fungal biomass was transferred into ethanol at a ratio of one volume of culture medium to two volumes of ethanol. The dye was extracted into the ethanolic phase by incubation at 4 .degree. C. and shaking for 16 hours. The liquid phase was decanted from the residual culture medium, and centrifuged at 3000 rpm for 10 min at 4 .degree. C.

The clarified extract (Extract A) was either stored for use, or purified further according to one of the procedures described under examples 2 and 3.

EXAMPLE 2

Purification of Extract A to Produce Extract B.

The crude ethanolic extract of Extract A produced according to the method described in example 1 was reduced in volume under high vacuum, chromatographed on cellulose powder using methanol as a solvent and applied to a sephadex LH-20 column, also eluted with methanol. Fractions were collected over 48 hours and the purple band eluting near the end was collected. This fraction was freeze dried and resuspended in a minimum volume of (0.1% acetic acid) methanol and stored.

EXAMPLE 3

Purification of 5,6-dihydro-3-[(1Z,4E,6E,8E)-1-hydroxy-3-oxo-1,4-,6,8-decatetraenyl]-6-hydroxymethyl-9a-methyl-2H-furo[3,2-g][2]benzopyran—2-9(9aH)-dione.

Extract B produced according to the method described in example 2 was subjected to HPLC purification (Supelco C16-amide column, resolved in 75% methanol/water, 0.05% acetic acid, then 50% acetonitrile/water, 0.05% acetic acid). The final fraction was frozen (−20 .degree. C.) to remove water and the remaining acetonitrile was evaporated under a stream of nitrogen.

This procedure produced analytically pure 5,6-dihydro-3-[(1Z,4E,6E,8E)-1-hydroxy-3-oxo-1,4,6,8-decatetraenyl]-6-hydroxymethyl-9a-methyl-2H-furo[3,2-g][2]benzopyran-2-9(9aH)-dione which was an orange solid.

EXAMPLE 4

Structure determination of 5,6-dihydro-3-[(1Z,4E,6E,8E)-1-hydroxy-3-oxo-1,4,6,8-decatetraenyl]-6-hydroxymethyl-9a-methyl-2H-furo[3,2-g][2]benzopyran-2-9(9aH)-dione The compound produced according to example 3 was analysed using a combination of NNR spectroscopy and high resolution mass spectrometry to determine the structure of, 6-dihydro-3-[(1Z,4E,6E,8E)-1-hydroxy-3-oxo-1,4,6,8-decatetraenyl]-6-hydroxymethyl-9a-methyl-2H-f-uro[3,2-g][2]benzopyran-2-9(9aH)-dione.

Nuclear Magnetic Resonance Spectroscopy.

The NMR sample was prepared by dissolving the HPLC purified compound obtained from Example 3 (.about. 5 mg) in CDCl$_3$(0.5 mL; 99.96 atom %, Aldrich) and filtering it into an NMR tube (PP527, Wilmald). The sample was degassed and equilibrated under an atmosphere of nitrogen.

The NMR data were acquired on a Bruker DRX600 (600 MHz) NMR spectrometer at 27 .degree. C. and processed using xwinNMR (version 2.6; Bruker). All 2D NMR experiments were run with quadrature detection with an $^1$H spectral width of 6009 Hz and a recycle delay of 2 s. Chemical shifts were referenced to the residual CHCl$_3$ (dH 7.26 ppm; dC 77.01 ppm). High power $^1$H p/2 pulses were determined to be 9.5 ms and low power (for MLEV spin lock) at 25.15 ms. $^{13}$C high power p/2 pulse was 10.5 ms and a low power pulse of 65 ms was used for GARP decoupling. Gradient pulses were delivered along the z-axis using a 100 step sine program.

Data for 1 D experiments were acquired using 32 K real points and zero filled to 64 K and then Gaussian multiplied for resolution enhancement. Carbon-hydrogen correlation (HSQC) was achieved via a sensitivity enhanced double INEPT transfer using echo/antiecho-TPPI gradient (80:20.1) selection (Palmer, A. G., III, Cavanagh, J., and Wright, P. (1991) J. Magn. Reson. 93, 151-70; Schleucher, J., Schwendinger, M., Sattler, M., and Schmidt, P. (1994) J. Biomol. NMR 4, 301-6; Kay, L. E., Keifer, P., and Saarinen, T. (1992) J. Am. Chem. Soc. 114(26), 10663-5). 2K data points were collected in t2 (128 scans per increment) with a 1.3 s recycle delay with decoupling during acquisition. In t1, 512 increments were used (10-170 ppm) and the INEPT sequence was optimized for a X—H coupling of 145 Hz. A gradient ratio of 80:20.1 was used to select echo/antiecho-TPPI phase sensitivity.

One dimensional ROESY spectra were measured using a selective Gaussian pulse on the proton of interest (Kessler, H., H. Oschkinat, C. Griesinger & W. Bermel, (1986) J. Magn. Reson. 70, 106; Stonehouse, J. P. Adell, J. Keeler & A. J. Shaka, (1994) J. Am. Chem. Soc. 116, 6037; Stott, K. J. Stonehouse, J. Keeler, T. L. Hwang & A. J. Shaka, (1995) J. Am. Chem. Soc. 117, 4199 4200). A 1000 step Gaussian program (60 ms, 64.6 dB) was used to achieve a p/2 pulse. A mixing time of 100 ms (13 dB) was used for a continues wave spin lock. Gradient selection was achieved with a 15% gradient along the z-axis. 10K transients were accumulated over 6009 Hz. ROE enhancements were measured as a percentage of the irradiated peak and not compensated for offset from the carrier frequency.

Two dimensional homonuclear Hartman-Hahn transfer spectra (TOCSY) were measured using the MLEV17 (Bax, A., & Davis, D. G. (1985) J. Magn. Reson. 63(1), 207-13) pulse sequence flanked with 2 ms low power trim pulses. Sine bell shifted (90°) apodisation was used in the processing of both dimensions.

2D$^1$H—$^{13}$C correlation via heteronuclear zero and double quantum coherence optimized for long range couplings (HMBC) with low-pass J-filter (145 Hz) to suppress one-bond correlations (Bax, A., & M. F. Summers, (1986) J. Am. Chem. Soc. 108, 2093-2094) was acquired with no decoupling during acquisition time and using gradient pulses (50: 30:40.1) for selection. The delay for evolution of long range couplings was optimized for couplings of 20, 10, 5 and 2 Hz in separate experiments. A spectral width of 210 ppm was used in F1 and the final spectrum magnitude calculated to destroy phase information.

$^1$H NMR (600 MHz, CDCl$_3$) δ1.75, s, C9a-Me; 1.84, dd, J 6.7, 1.1 Hz, C9'-Me;2.80, dd, J 17.2, 3.6 Hz, H5α; 2.89, ddd, J 17.1, 11.5, 1.9 Hz, H5β.; 3.85, dd, J 12.2, 5.5 Hz, C6CH$_2$OH; 3.97, dd, J 12.2, 3.4 Hz, C6CH$_2$OH; 4.39, m, H6; 5.97, m, H9'; 6.10, d, J 15.1 Hz, H4', 6.19, ddd, J 15.1, 10.6, 1.6 Hz, H8'; 6.25, dd, J 14.6, 11.2 Hz, H6'; 6.58, dd, J 14.5, 10.5 Hz, H7'; 6.79, s, H2'; 7.16, bs, H4, 7.32, dd, J 15.2, 11.2 Hz, H5'; 7.85, s, H8.

$^{13}$C NMR (125 MHz, CDCl$_3$) δ 18.8, C9'-Me; 28.0, C9a-Me; 29.3, C5; 63.4, C6-CH$_2$OH; 79.0, C6; 86.2, C9a; 101.0, C2'; 112.2, C8a; 113.4, C4; 115.3, C3; 126.5, C4'; 128.6, C6'; 131.7, C8'; 136.0, C9'; 140.9, C4a; 142.0, C7'; 142.6, C5'; 159.0, C8; 168.2, C2/C3a; 177.7, C1'; 185.0, C3'; 190.0, C9.

Heteronuclear single quantum coherence (HSQC) was used to correlate and assign all protons to protonated carbons. In addition, each spin system was characterised by running a series of total correlation spectroscopy (TOCSY) experiments with mixing times of 8 msec, 20 msec, 100 msec. The shortest mixing time gave correlations to only the directly coupled protons whereas the longest mixing time identified the entire spin system and gave information about very small long range couplings which were valuable for assigning the positions of the many (apparently) uncoupled protons. Thorough space connectivities were achieved by a series of one dimensional selective rotating frame correlation spectroscopy (ROESY) experiments. Selective excitation was achieved by a low power Gaussian 90 degree pulse and using gradient section to observe only ROE's free of TOCSY transfers. A mixing time of 100 msec was found to be optimal. Long range heteronuclear multiple quantum coherence (HMBC) spectra with mixing times of 25, 50, 100 and 250 msec was found to be essential to assign all non-protonated carbons. Even after this, C2 was found not to correlate with any protons and was coincident with C3a at 168.2 ppm.

From the spectral data, several tricyclic skeletons were theoretically possible but one (6-dihydro-3-[(1Z,4E,6E,8E)-1-hydroxy-3-oxo-1,4,6,8-decatetraenyl]-6-hydroxymethyl-9a-methyl-2H-f-uro[3,2-g][2]benzopyran-2-9(9aH)-dione), fitted the available data exactly.

Mass Spectrometry

The compound produced according to Example 3 was subjected to high resolution mass spectrometry to determine that the molecular formula of the compound was $C_{23}H_{22}O_7$.

Mass spectrum (ESI, positive ion) m/e 411 (M+H$^+$, 55%), 317 (5), 249 (12), 163 (10), 121 (100), 93 (4). Negative ion ESI-FTICR Found: M−H$^+$, 409.1304, $C_{23}H_{21}O_7$ requires 409.1293; found: 247.0617, $C_{13}H_{12}O_5$ requires 247.0685.

$\lambda_{max}$ and $\nu_{max}$ $\lambda_{max}$ (MeOH) 432, 555 nm, ε10000, 4000. $\lambda_{max}$(alkaline MeOH) 432 nm, ε16000. $\lambda_{max}$ (acidic MeOH) 390, 560 nm, ε6000, 10000.

$\lambda_{max}$ (neat) 3400 (br), 2925, 2854, 1744, 1712, 1589, 1259, 1010 cm$^-$.

EXAMPLE 5

Protein Gel Staining Using Extract A.

A protein gel was prepared according to any one of a number of standard protocols. For example, an SDS page gel was prepared according to the protocol of Laemmli (U.K. 1970, Nature, 227:680-685). After electrophoresis was completed, the gel was removed from the electrophoresis apparatus. The gel was fixed in a container containing 100 mL of a staining solution composed of 90 mL water, 10 mL glycerol and 5 mL of Extract A. The gel and staining solution were incubated with gentle shaking for 90 minutes. After the 90 minute staining procedure, the solution was removed and the gel briefly washed three times in water. After these brief washes, the gel was placed in 100 mL of 10% glycerol in water and incubated with shaking for a further 30 min.

To visualise the proteins in the gel, the gel was transferred to a UV transilluminator (307 nm), and photographed using polaroid 667 black and white film and a filter set designed for the detection of ethidium bromide gels (eg. Molecular probes E-7591).

EXAMPLE 6

Epifluoroescence Differentiation of Sporulated and Vegetative Cells.

A micro-organism is cultured under conditions to promote sporulation and Extract B is used to facilitate the identification of sporulated cells within a predominantly vegetative cell culture. For example, Saccharomyces cerevisiae was grown in a water based broth containing 10 g/L Glucose, 5 g/L yeast extract, and 10 g/L peptone. After a 16 hour incubation at 30 .degree. C., the cells were harvested by centrifugation and resuspended in 1 mL of water. The 5 .mu.L aliquots of the culture were spotted onto a semi-solid medium composed of 5% Potassium acetate, 2% Agar and water. The cultures were incubated at 22 .degree. C. for 4 days to allow sporulation of the yeast cells. The sporulated culture was resuspended in water to a density of 1.times.10$^9$ cells per mL. 5 . mu.L of Extract B was added to 1 mL of the sporulated culture. To counterstain, 5 .mu.L of a 10 mM solution (in DMSO) of 5(6)-carboxyfluorecein diacetate (CFDA), was added to the sporulated culture. After 5 minutes, the sporulated culture was harvested by centrifugation and resuspended in 1 mL of water. Examination under an epifluorescence microscope (excitation 488 nm) allowed for rapid differentiation between sporulated and vegetative cells.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A compound having the stereochemistry depicted in formula (Ib), including tautomers thereof:

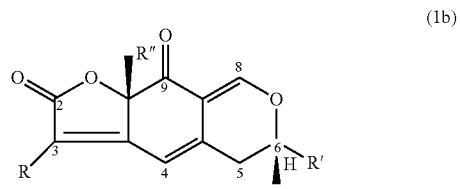

(Ib)

wherein R is a straight or branched chain $C_{1-20}$ conjugated alkenyl group optionally substituted with hydroxy and oxo groups; R' is a straight or branched chain $C_{1-20}$ alkyl group optionally substituted with a hydroxy group and R" is a straight or branched chain $C_{1-20}$ alkyl group, including tautomers thereof and wherein the compound of formula Ib when it interacts with bovine serum albumin (BSA) fluoresces at a broad range of wavelengths.

2. A compound according to claim 1, wherein R is —C(OH)CHC(O)(CH)$_6$CH$_3$ R' is —CH$_2$OH and R" is Me being the compound 5,6-dihydro-3-[(1Z,4E,6E,8E)-1-hydroxy-3-oxo-1,4,6,8-decatetraenyl]-6-hydroxymethyl-9a-methyl-2H-furo[3,2-g][2]benzopyran-2-9(9aH)-dione according to formula (Ic), including tautomers thereof:

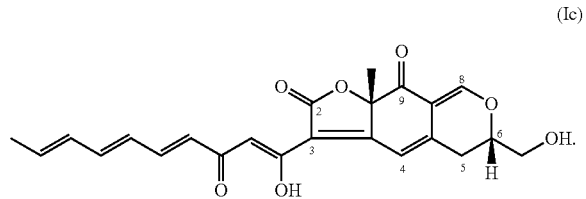

(Ic)

\* \* \* \* \*